US008463568B1

(12) United States Patent
Wynn

(10) Patent No.: US 8,463,568 B1
(45) Date of Patent: Jun. 11, 2013

(54) MEASURING SEAWATER CAPACITANCE IN THREE DIMENSIONS AS WELL AS TIME

(75) Inventor: Jeffrey C. Wynn, Camas, WA (US)

(73) Assignee: The United States of America, as represented by the Secretary of the Interior, Washington, DC (US)

( * ) Notice: Subject to any disclaimer, the term of this patent is extended or adjusted under 35 U.S.C. 154(b) by 298 days.

(21) Appl. No.: 13/091,314

(22) Filed: Apr. 21, 2011

(51) Int. Cl.
*G01R 25/00* (2006.01)
*G01V 3/06* (2006.01)

(52) U.S. Cl.
USPC ............................................. 702/65; 324/362

(58) Field of Classification Search
USPC .. 702/65, 1–2, 57, 64, 72, 127, 189; 324/358, 324/362, 364–365
See application file for complete search history.

(56) References Cited

U.S. PATENT DOCUMENTS

| | | | |
|---|---|---|---|
| 3,182,250 A | | 5/1965 | Mayes |
| 4,434,364 A | * | 2/1984 | Correa et al. ................ 250/253 |
| 4,617,518 A | | 10/1986 | Srnka |
| 6,236,211 B1 | | 5/2001 | Wynn |
| 6,236,212 B1 | | 5/2001 | Wynn |
| 7,002,350 B1 | | 2/2006 | Barringer |
| 7,132,831 B2 | | 11/2006 | Brabers |
| 7,471,089 B2 | | 12/2008 | Zerilli et al. |
| 2001/0030539 A1 | | 10/2001 | Montgomery et al. |

OTHER PUBLICATIONS

Wynn, J.C., and D.D. Snyder, 2010, Comment on "Benefits of the induced polarization geoelectric method to hydrocarbon exploration" (P. Veeken, P.J. Legeydo, Y.A. Davidenko, E.O. Kudryavceva, S.A. Ivanov, and A. Chuyaev, 2009, Geophysics, 74, No. 2, B47-B59): Geophysics, 75, No. 1, Jan.-Feb. 2010, X1-X2.

Veeken, P.C.H., P.J. Legeydo, Y.A. Davidenko, E.O. Kudryavceva, S.A. Ivanov, and A. Chuyaev, 2009, Benefits of the induced polarization geoelectric method to hydrocarbon exploration: Geophysics, 74, No. 2, Mar.-Apr. 2009, B47-B59.

Wynn, J.C. and J.F. Giller, 2008, Field demonstrations in anthropogenic waste or unexploded ordnance sought for USGS marine induced polarization (IP) streamer system technology: USGS Fact Sheet, Sep. 2008, 4 pages. http://pubs.usgs.gov/misc_reports/ipstreamer/IP-Streamer_Wynn-Giller.pdf.

Technos, Inc., 2004, Surface geophysical methods: Technos, Inc. Newsletter, 1, No. 1, Fall 2004, 20 pages. http://www.technos-inc.com/pdf/SurfaceTechnotes.pdf.

(Continued)

*Primary Examiner* — Toan Le
(74) *Attorney, Agent, or Firm* — C. Joan Gilsdorf

(57) ABSTRACT

A system for mapping and characterizing a hydrocarbon plume in seawater by measuring seawater capacitance. Multiple streamer cables are towed in the sea behind a ship, each at a different depth, simultaneously. Each streamer cable includes transmitters and receivers at the free end thereof. The free ends of the streamer cables pass through the plume and the transmitters transmit an electrical current into the plume. The receivers detect any secondary signals produced by capacitive effects of the hydrocarbon or hydrocarbon and dispersant surrounded by conductive seawater in response to the inducing electrical current. Pre-amplifiers connected to the receivers and a two-step calibration procedure and various grounding and shielding steps provide noise rejection. An electronics system on board the ship processes the secondary signals to provide immediate development of detailed maps of plume location, and to provide tracking and characterization of how the plume changes shape and character over time.

22 Claims, 4 Drawing Sheets

OTHER PUBLICATIONS

Wynn, J.C., 1988, Titanium geophysics—the application of induced polarization to sea-floor mineral exploration: Geophysics, 53, 386-401.

Wynn, J.C., and Grosz, A.E., 2000, Induced polarization—a tool for mapping titanium-bearing placers, hidden metallic objects, and urban waste on and beneath the seafloor: Journal of Environmental and Engineering Geophysics, 5, No. 3, 27-35.

Wynn, J.C., and Roberts, Will, 2009, The application of induced polarization techniques to detect metal-bearing offshore anthropogenic waste and unexploded ordnance: Proceedings of the Symposium for the Application of Geophysics to Environmental & Engineering Problems, Ft. Worth, TX, Mar. 29-Apr. 2, 2009, 1104-1113.

* cited by examiner

“MEASURING SEAWATER CAPACITANCE IN THREE DIMENSIONS AS WELL AS TIME

STATEMENT OF GOVERNMENT INTEREST

The invention described herein may be manufactured, used, and licensed by or for the U.S. Government for governmental purposes without payment of any royalties thereon.

BACKGROUND

The present invention relates to rapidly mapping and characterizing hydrocarbon and dispersant plumes in seawater.

In April 2010, the Deepwater Horizon oil drilling rig exploded, causing an oil spill at the Macondo Well in the Gulf of Mexico that was one of the largest accidental marine oil spills in the history of the petroleum industry. The well released over 200 million gallons of crude oil into the Gulf of Mexico, resulting in damage to marine and wildlife habitats and to fishing and tourism industries, as well as health concerns to inhabitants of the Gulf coastline. Although the well was eventually capped, the impact of this massive spill continues today, and will continue for years to come.

Masses of undersea oil, which have lengths spanning tens of miles, have been reported in the Gulf of Mexico. These oil or hydrocarbon plumes, plus the vast quantities of toxic chemicals (such as COREXIT oil spill dispersants by Nalco Company) intended to disperse them, move and spread in the Gulf seawater column, posing long-term threats to marine and coastal wildlife. The volatile components of the plumes floated to the surface early, where they could be burned off, but the vast majority of the oil either sank (smothering life on the seafloor) or drifted away with the Gulf Loop Current.

Such a huge and amorphous target is extremely expensive and difficult to accurately characterize. Determining the character of a hydrocarbon plume currently requires stopping a $100,000-per-day ocean-going vessel in the water for several hours, and dropping sampling bottles over the side to depths in excess of a mile. Only an extremely tiny sample of the water column is collected, which must then be analyzed later in a laboratory, adding days of additional time. The entire process operates under the implicit assumption that the oil plume does not move during the hours needed to do the sampling, which is not a valid assumption.

Other existing methods that can be used to map hydrocarbon plumes in seawater include sonic methods (e.g., side-scan sonar) and resistivity. However, sonic methods require a significant velocity contrast to function, and a dispersed hydrocarbon plume will have a sound velocity indistinguishable from unpolluted seawater, rendering this approach ineffective away from the erupting seafloor well-head. Resistivity methods will not work because the sampling current will short-circuit past the oil droplets following the path of least electrical resistance through the highly-conductive seawater, rendering this approach equally ineffective.

Besides the Macondo Well blowout, there have been a number of other major well-blowouts and oil leaks in the open ocean, including several larger than the Macondo Well event. Notable among these are the Ixtoc Well (Bay of Campeche, 1979) and the Persian Gulf (1991), which each released larger volumes of oil. At this time, there is no way to really know what remains from these huge pollution events, since divers can rarely descend below 100 meters, and people controlling remotely-operated underwater vehicles can see little more than divers in low-visibility, dark waters.

Also, there are over 6,600 active or removed oil platforms in the Gulf of Mexico alone, and each connects to a huge network of pipelines lying on or just below the seafloor. These pipelines convey oil from all the current and former offshore oil platforms and wells to collection points and refineries on land. Many of these pipelines are old, corroded, or damaged by hurricanes, and are known to be leaking. In addition, the Gulf of Mexico has many natural oil seeps.

To protect coastline and marine environments, new technologies are needed to detect, map, and characterize undersea hydrocarbon plumes, and to predict their movements.

SUMMARY

Induced polarization (IP) is a general term for a surface-sensitive physical phenomenon caused by several different electrochemical mechanisms, but all behave like a capacitance. On land, an induced voltage injected into the ground can cause ions in groundwater to adsorb onto sulfide mineral grains such as pyrite and chalcopyrite. When the inducing voltage is released, the accumulated charge bleeds back off, and this can be measured. This phenomenon is called "polarization" or "chargeability." A large volume of rock filled with disseminated copper sulfides and pyrite (or clay) will behave as a large capacitive system to an IP transmitter-receiver array energizing the ground surface above it.

A simple capacitor can be characterized as two conductive plates separated by a resistive, dielectric material such as oil. It is used in electronic systems to delay a signal or to store charge in a power supply. A dispersed plume of oil droplets and blobs immersed in a highly conductive medium such as seawater is topologically equivalent to a simple capacitor. Therefore, a dispersed hydrocarbon plume presents a large surface area of oil-to-seawater, and is a strong polarizer, an anomaly in a sea that otherwise has no chargeability. The greater the dispersal of the hydrocarbons, the greater the polarizing surface area exposed to seawater for the same amount of oil, and the greater the subsequent chargeability. The size of a capacitor and strength of the dielectric between its plates also controls the rapidity of charge bleed-off, thus from basic physics, an oscillating induced voltage signal in polluted seawater causes a varying response with frequency depending on the size of the oil droplets (i.e., smaller droplets yield a higher frequency for peak response, and the more surface area exposed to seawater, the greater the volume capacitance).

In accordance with the invention, there is provided a seawater capacitance detection system and method that allows users to rapidly map hydrocarbon plumes in seawater in four dimensions: three spatial dimensions as well as how the plumes evolve and move over time. The measurement of plume movement over time allows future plume evolution to be reliably predicted. A towed electrical transmitter-sensor streamer array having three or more streamer cables is pulled through the water column at three or more depths to detect hydrocarbons in the seawater column by measuring seawater capacitance. This permits immediate development of detailed maps of where a pollutant plume is located, as well as the tracking and characterization of the plume over time. In a synoptic view, the streamer array can be towed in lawnmower fashion as fast as the host ship can travel, rapidly sampling and characterizing the hydrocarbon plume volume at multiple depths at the same time.

In accordance with one embodiment of the invention, there is provided a seawater capacitance detection method for rapidly mapping and characterizing hydrocarbon plumes in seawater. The method includes towing a streamer array having three or more vertically stacked streamer cables at three or more depths, respectively, through a seawater column. Two or more transmitter electrodes and a plurality of receiver electrodes are placed on each streamer cable. Transmitter electrodes transmit an electrical current into the seawater. Transmission of the electrical current signal is episodically terminated, and the receiver electrodes measure the returned secondary signals produced in response to terminating transmission of the electrical current signal. The returned secondary signals indicate the presence of a hydrocarbon plume in the seawater if their capacitance is not zero. Based on the returned secondary signals, a capacitance value is calculated for discrete volume points within the hydrocarbon plume and seawater mixture sampled by the receiver electrodes. The hydrocarbon plume is then mapped and characterized using the capacitance values.

In accordance with another embodiment of the invention, there is provided a seawater capacitance detection method for rapidly mapping and characterizing hydrocarbon plumes in seawater. The method includes towing a streamer array having three or more vertically stacked streamer cables at three or more depths, respectively, through a seawater column containing a hydrocarbon plume. Two or more transmitter electrodes on each streamer cable are energized with an electrical current signal, the transmitter electrodes injecting electrical current into the seawater column. A plurality of receiver electrodes are arranged on each streamer cable into one or more receiver sets. Transmission of the electrical current signal is episodically turned off. Each receiver set samples a volume of seawater surrounding it and detects any returned secondary signals produced by a capacitive effect resulting from injecting the electrical current into the seawater column and turning off the transmission of the electrical current signal. Each receiver set successively samples a larger volume of water as the receiver sets are positioned further away from the transmitter electrodes. The returned secondary signals are processed, for each adjacent pair of receiver sets, by subtracting the smallest volume of seawater from the next smallest volume of seawater to yield a capacitance value of a donut-shaped sampling volume of seawater outside the smallest volume. The receiver sets positioned further away from the transmitter electrodes provide increasingly larger donut-shaped sampling volumes of sampling data of the capacitance of the seawater column through which the streamer cables are towed. The capacitance values of the donut-shaped sampling volumes of seawater are processed and geometrically corrected to yield a frequency-varying final seawater capacitance value for the volume of seawater sampled by each receiver set. The hydrocarbon plume is then mapped and characterized using the final seawater capacitance values of the receiver sets.

In accordance with another embodiment of the invention, there is provided a seawater capacitance detection method for rapidly mapping and characterizing hydrocarbon plumes in seawater. The method includes towing a master streamer cable through a seawater column, and attaching a sled to an end of the master streamer cable to maintain it substantially vertical in the seawater column. A plurality of parasitic streamer cables are attached to, and extend from, the master streamer cable. Each parasitic streamer cable samples different depths simultaneously. Two or more transmitter electrodes and a plurality of receiver electrodes are placed on each parasitic streamer cable. The transmitter electrodes transmit an electrical current into the seawater. Transmission of the electrical current signal is episodically terminated, and the receiver electrodes measure any returned secondary signals produced in response to terminating the transmission of the electrical current signal. A non-zero capacitance value of the returned secondary signals indicates the presence of a hydrocarbon plume in the seawater. Based on the returned secondary signals, a capacitance value is calculated for discrete volume points within the hydrocarbon plume and seawater mixture sampled by the receiver electrodes. The hydrocarbon plume is then mapped and characterized using the capacitance values.

BRIEF DESCRIPTION OF THE DRAWINGS

Various aspects and advantages of the invention will become apparent from the following detailed description, taken in conjunction with the accompanying drawings. The drawings are not necessarily drawn to scale. In the drawings.

DETAILED DESCRIPTION OF THE PREFERRED EMBODIMENTS

Figure 1:
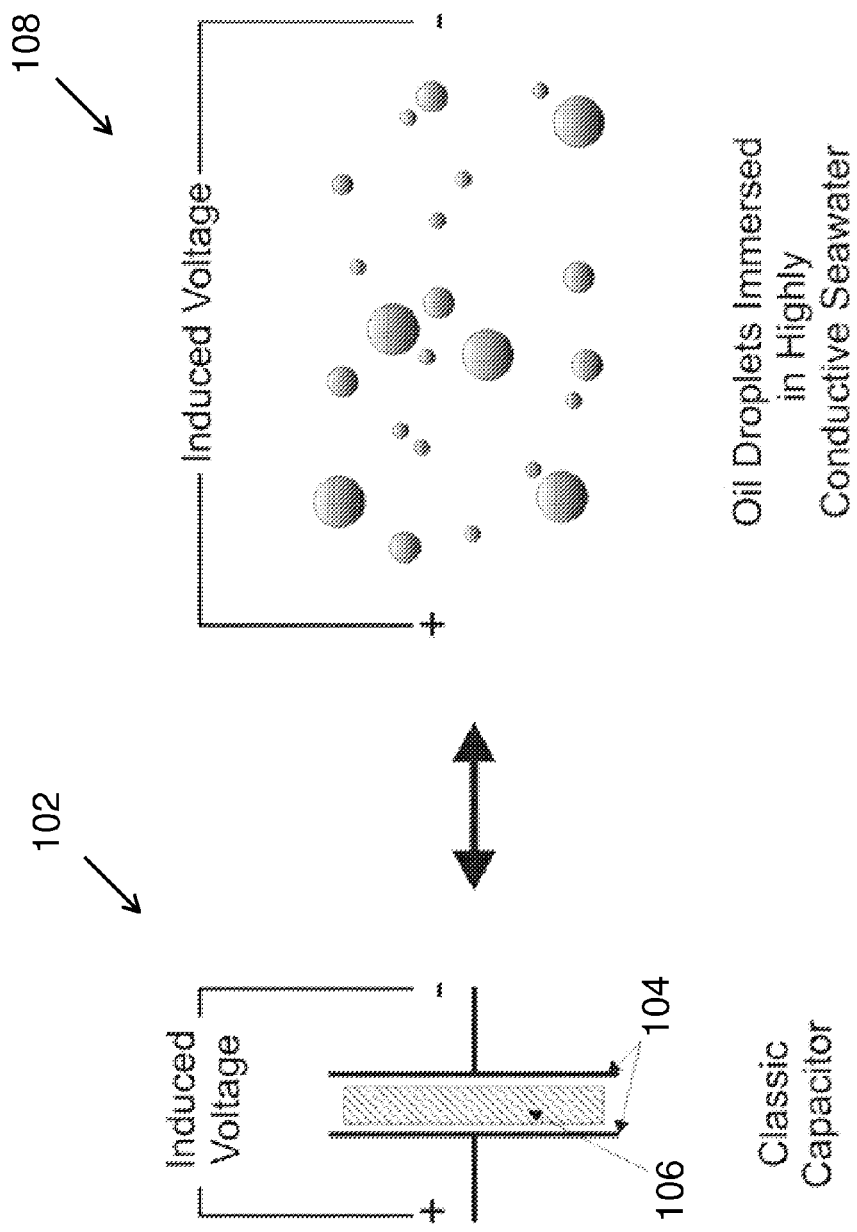
FIG. 1 is a conceptual schematic diagram for explaining the topological equivalence of a classical capacitor and dispersed hydrocarbons in highly conductive seawater according to an exemplary embodiment of the invention.

The induced polarization (IP) method has been used for decades to detect certain minerals and clays that give rise to an IP effect in the ground or beneath the seafloor. A system and a method that use the IP method to detect minerals and clays in the seafloor are disclosed in U.S. Pat. No. 6,236,211 and in U.S. Pat. No. 6,236,212, both issued May 22, 2001, and both hereby incorporated by reference in their entirety. The typical IP method involves injecting an electrical current (through an induced voltage) into the subsurface. Electrochemical reactions occur between the minerals and surrounding water, causing the minerals to act as capacitors. While the current is on, electrical energy is stored. After the current is turned off, the stored energy is discharged, which causes current to flow from the minerals back to the water in which they are immersed. This method is used to measure the slow decay of voltage in the ground or subsurface—if a polarizer is present—after the current is turned off. Induced polarization is a phenomenon that can have several electrochemical causes, but all of them are capacitive in character and behavior, and all are sensitive to surfaces exposed to water rather than to volume. The invention described herein proposes a new physical phenomenon causing an IP-like effect, and proposes how to measure it.

One manifestation of the IP response of a subsurface polarizer is that the voltage on an array of detectors or receivers lags the primary or inducing voltage (produced by a transmitter dipole pair, described below) by a finite amount of time. This is always expressed as a phase-shift (i.e., a slight time-shift or lag of the wave-cycle between the transmitter and the receiver). The delay phenomenon is based on a complex interaction of ions in the electrolyte (the ground water) with the individual mineral surfaces. Because of this, IP is more sensitive to surface area than to volume, and is thus ideally suited for dispersed or disseminated targets.

An IP survey typically gathers both resistivity information, which is generally a measure of the porosity of the substrate, as well as polarization information, which is a measure of the reactivity or "chargeability" of certain minerals disseminated throughout the subsurface. Computer modeling is then used to arrive at models that best fit the observed data acquired on the land surface or at the seafloor, with the purpose of providing a true map of the three-dimensional nature of the underlying subsurface.

Evidence in the scientific literature (and found in public news media) after the Macondo Well erupted in the Gulf of Mexico in April 2010 indicated that the oil sampled in the seawater was not pure oil. It was always a mixture of hydrocarbons and saltwater, except where it accumulated on the coast and became subsequently dehydrated. Instead, the hydrocarbon pollution has been described as "dispersed" in the seawater. In other words, the oil was found in blobs and tiny droplets, each surrounded by conductive seawater, with the aggregate forming a vast cloud. In the invention disclosed herein, the strength and frequency response to such a mixture correlates closely with the surface area exposed to the seawater and the size-distribution of the droplets.

As shown in FIG. 1, a simple capacitor 102 can be characterized as two conductive metal plates 104 separated by a resistive dielectric medium 106, commonly a chemically-doped oil. Oil dispersed as droplets and blobs in highly conductive seawater 108 is topologically equivalent to the simple capacitor 102 where the highly conductive seawater substitutes for the metal plates, and seafloor hydrocarbon seeps and hydrocarbon plumes in the water column, such as the Macondo Well output, are the oil/dielectric. In both cases, an inducing voltage can cause charge to be stored. When the transmitted inducing voltage is turned off, the charge will bleed back in a manner that can be measured at receiver electrodes. Therefore, a hydrocarbon plume in seawater is polarizable and behaves as a frequency-dependent capacitance to a chargeability-measuring array passing through the plume.

In essence, the dispersed oil plume is a giant, amorphous capacitor, with capacitance changing over spatial and time dimensions according to the movement, overall density, and droplet size distribution of the hydrocarbons present. There will be discrete different capacitance values according to droplet size—oil dispersed as smaller droplets will have greater volume capacitance. However, the capacitance values will be distributed because there will normally be a range of different droplet sizes in any hydrocarbon plume in the open ocean. The capacitance frequency-response will also vary according to droplet size—smaller droplets will have a higher frequency response (i.e., a faster bleed-back rate). A resistivity survey cannot detect hydrocarbon plumes and seeps in the seawater column because of their distributed nature. In other words, the measuring electrical current will short-circuit around the oil, following the path of least electrical resistance in the conductive seawater. Sonic methods will likely not detect a dispersed hydrocarbon plume for a similar reason—there is no significant velocity contrast.

Seawater has previously been considered a homogenous conductive medium. It almost always is homogenous because it is constantly mixing. Salinity and temperature may vary modestly in enclosed seas depending on depth and surface evaporation, but the sea has always been treated as no more than an electrically-conductive medium with biological content. Scientists would not normally consider measuring capacitance in something that was uniformly conductive—this would be like trying to classify colors in the dark. There is no capacitance in a metal wire or single metal plate. The system and method of the present invention, as described below, provides a way to measure seawater capacitance, such that hydrocarbon plumes in seawater can be mapped and characterized. The system and method described herein does this by measuring a multi-frequency phase-shift between transmitted and received signals (i.e., measuring a capacitance-caused time-lag between transmitter and receiver signals over a wide frequency range) to map and characterize hydrocarbons in seawater. In an electronic circuit, a capacitor causes a time-delay in the signal. The present invention uses this broadband signal time-lag to measure variations in, and characterize the frequency-dependent capacitance of, the seawater column, which is now described in greater detail.

Figure 2:
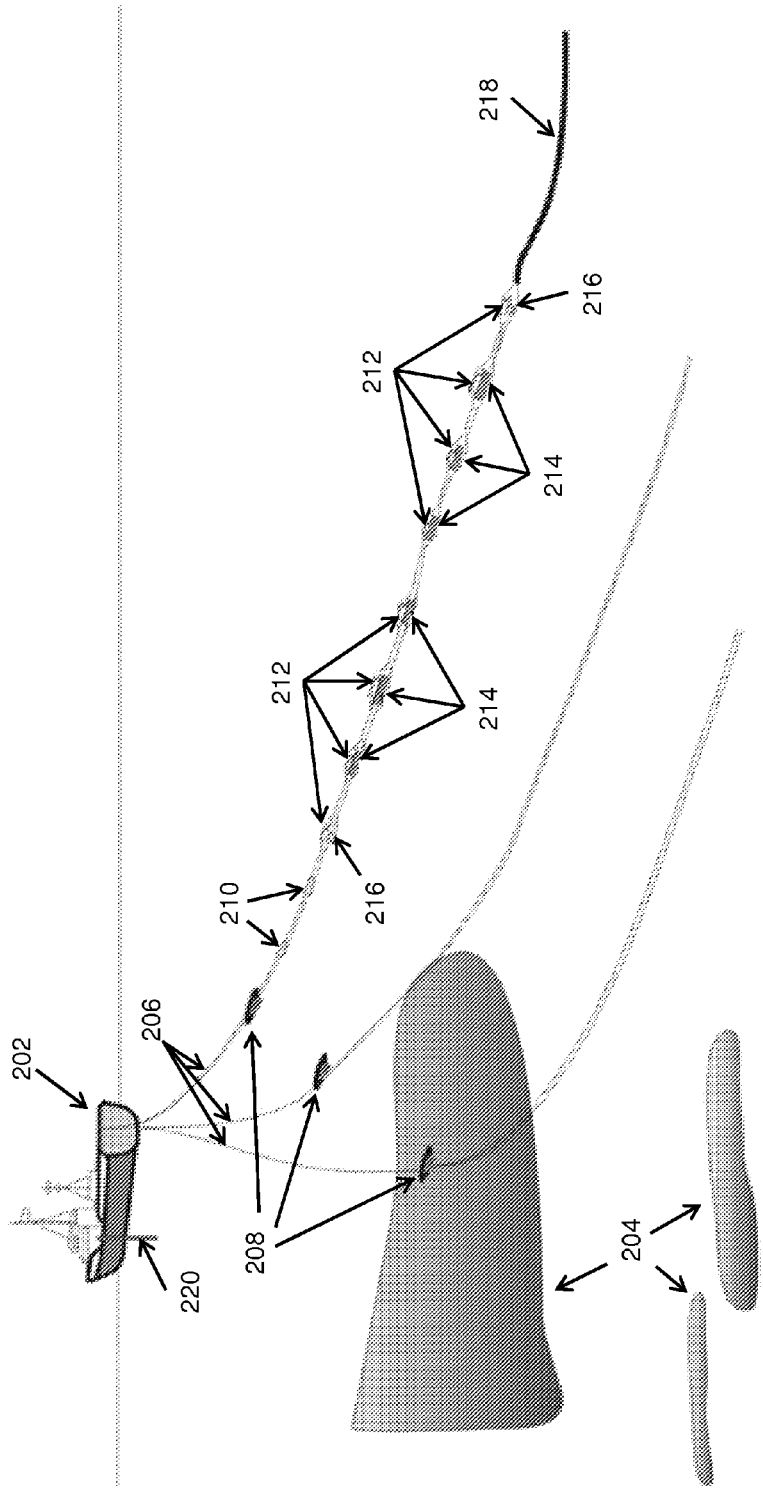
FIG. 2 is a schematic perspective view of a ship towing an array of multiple, vertically-stacked streamer cables through an undersea hydrocarbon plume in accordance with an exemplary embodiment of the invention.

Referring to FIG. 2, a ship 202 is used to tow a multi-component streamer array through seawater containing hydrocarbon plumes and plume stringers 204. The streamer array includes a series of multi-wire-stranded streamer cables 206. Preferably, between three and ten parallel streamer cables 206 are towed behind the ship 202 in a vertically stacked array. Three such streamer cables 206 are illustrated in the embodiment shown in FIG. 2. Each streamer cable 206 has multiple components, including depth-control cable depressors 208, transmitter electrodes 210, receiver electrodes 212, pre-amplifiers 214, a depth-sensing pressure transducer with an acoustic transponder (herein a "pressure transducer/acoustic transponder unit") 216 located at the peripheral and distal ends of each streamer cable 206, and a drogue 218. For ease of illustration, the multiple components are shown only on the first or top streamer cable 206. The streamer cables 206 are similar to one another, except the deeper-riding cables may be longer than the shallower-riding cables.

Each streamer cable 206 samples different depths and volumes of seawater at the same time. The depth-control cable depressors 208 maintain the depth of each streamer cable 206. Each depth-control cable depressor 208 can be a small sled with adjustable fins or farings, for example, and may either be remotely adjustable or preset for a particular depth. The ship 202 includes a commercially-available three-dimensional (3-D) acoustic streamer element locator 220 deployed from the side of the ship 202 (described below), and an on-board control and signal processing system (described below and illustrated in FIG. 4). Each streamer cable 206 carries a transmitted signal from the control and signal processing system down the cable and returns an amplified received signal back to the control and signal processing system aboard the ship 202. Transmitted electrical energy does not travel very far in the highly conductive seawater of the ocean. For this reason, the streamer cables 206 are towed behind the ship 202 in a vertically-stacked array so more of the vertical water column may be sampled at the same time.

The pressure transducers/acoustic transponder units 216 are used to provide accurate real-time depth information for each streamer cable 206. The drogue 218, which may be something as simple as a knotted rope, is attached to the distal end of each towed streamer cable 206 for stabilization while underway. This minimizes cable whipping and undulation that would contribute an artificial electrical noise to the received signal (due to changing distances between transmitter and receiver dipoles, described below). The separation between streamer cables 206 is adjustable according to target depth-range to be mapped. In practical terms, the number of streamer cables 206 and target depth-range would be similar for most deep oceans such as the Gulf of Mexico, but would be modified (e.g., by using fewer streamer cables 206) for shallow coastal shelves.

Figure 3:
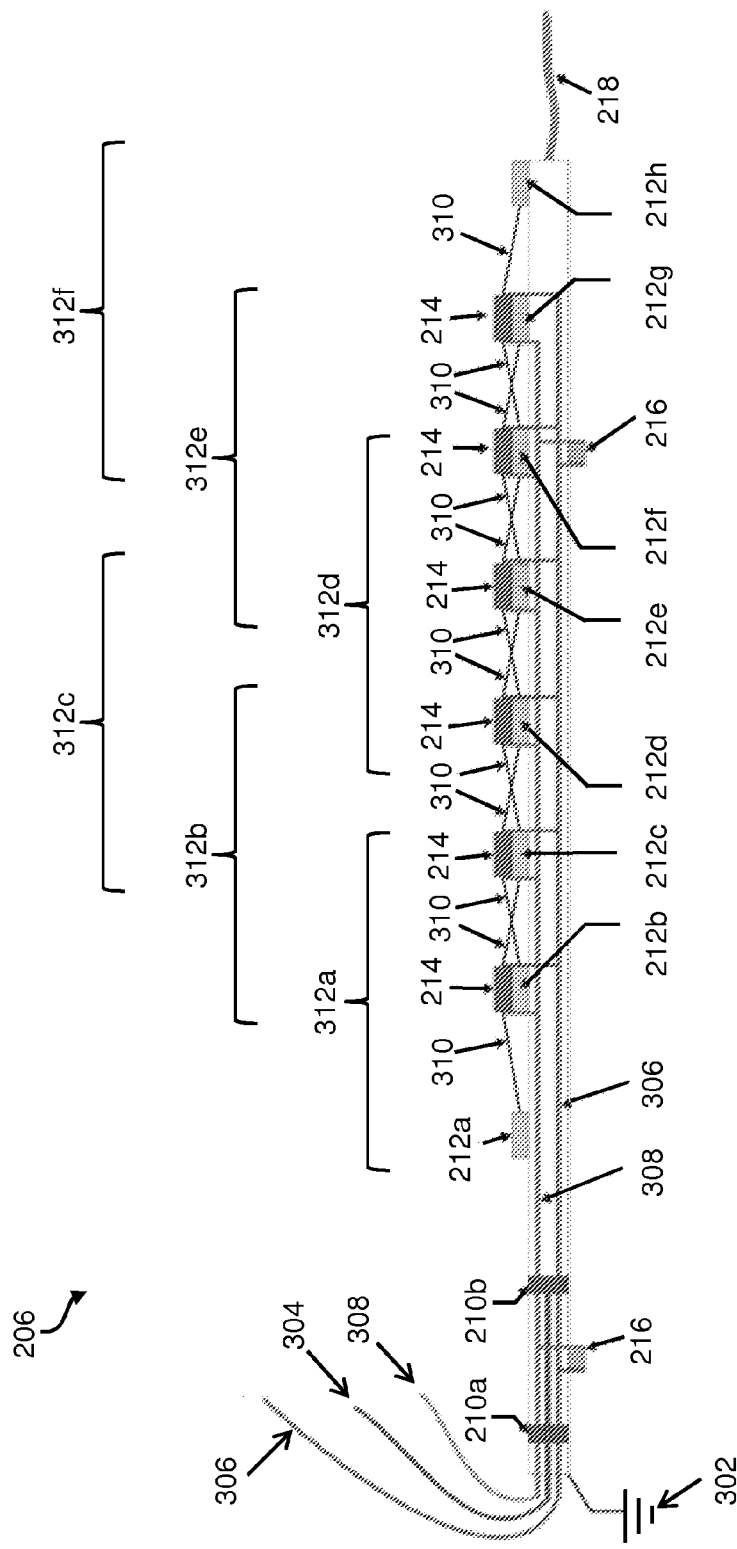
FIG. 3 is a schematic side view of the active portion of one of the streamer cables of FIG. 2, according to an exemplary embodiment of the invention.

FIG. 3 illustrates one of the streamer cables 206. In the embodiment shown in FIG. 3, each streamer cable 206 is shielded and independently grounded 302 against outside electrical noise. A transmitter cable 304 supplies power to the transmitter electrodes 210 (i.e., to a transmitter dipole). Preferably, the transmitter cable 304 is a ground-shielded, twisted-pair of low gauge (e.g., eighteen or lower gauge) wire designed to provide a square-wave current signal to the transmitter electrodes 210. A signal return cable 306 returns the received signal to the ship-board control and signal processing system. This data signal can be returned via either shielded coaxial wire cabling or optical fiber, depending on design considerations. A power supply cable 308 supplies power to the pre-amplifiers 214 and to the pressure transducer/acoustic transponder units 216. The power supply cable 308 is typically a high-gauge twisted pair of wires.

In the exemplary embodiment shown in FIG. 3, the streamer cable 206 carries a pair of the transmitter electrodes 210 (210a and 210b). The transmitter electrodes 210 are spaced typically 20-100 meters apart, depending on the depth-range of interest and practical considerations such as how much current a given streamer cable 206 can support without overheating due to internal resistance. The transmitter electrodes 210 are preferably made of coiled titanium wire to prevent corrosion when used with 10 or more amperes of electrical current. Seawater is highly corrosive, especially in the presence of several amperes of current. The transmitter electrodes 210 are used to transmit current at relatively high amperages and at low voltages to increase the signal-to-noise ratio. The transmitter electrodes 210 take advantage of a non-linear surface-effect transition at about 15 volts, above which current will easily cascade from the transmitter electrodes 210 into the seawater. The maximum current is then effectively limited only by the capacity of a current transmitter 404 (FIG. 4) on-board the ship 202 that sends the square wave to the transmitter electrodes 210 and the internal resistance of the transmitter cable 304. The transmitter electrodes 210 are connected to each streamer cable 206 by using waterproof "take-outs" (not shown) to prevent seawater from penetrating into the streamer cables 206 under hydrostatic pressure and changing the electrical characteristics of the streamer cables 304 while in use. In this regard, a change in the cable phase characteristics caused by water entry would degrade the effectiveness of the calibration procedure, and reduce the reliability of the measured towed-mode phase-values (described below).

The transmitter cable 304 provides a square-wave current signal to the titanium transmitter electrodes 210, while having minimum cross-talk with the received signal coming back up the streamer cable 206. The waveform of the transmitter signal is optimized to include a wide range of frequencies in order to detect a varying-frequency capacitance between dispersed hydrocarbons and the highly conductive seawater medium. Typically, this optimization means using a square-wave transmitter waveform, which is made up of multiple odd-frequency harmonics. A 1 Hz square wave is composed of 1st, 3rd, 5th, 7th, 9th, 11th, etc. sine-wave harmonics, which means a Fast Fourier Transform can extract frequencies of 1 Hz, 3 Hz, 5 Hz, 7 Hz, etc. from this single square waveform. The typical range of frequencies of a square wave used on land in an IP search for sulfide minerals is 0.1-10 Hz, while a range of about 1 to about 100 Hz is used in a seawater capacitance application.

In the embodiment shown in FIG. 3, eight receiver electrodes 212 (212a-212h) are affixed to each streamer cable 206 in an equally spaced relationship to provide sampling at different distances away from the streamer cable 206. As illustrated, the first or most proximal of the receiver electrodes 212a from the ship 202 is spaced at about one-half to about one times the transmitter dipole electrode separation away from the most proximal transmitter electrode 210a, and subsequent receiver electrodes 212b-212h are equally-spaced farther along the streamer cable 206. The actual numbers of transmitter and receiver electrodes and the distances separating the electrodes (called the dipole spacing) can be adjusted in conformance to the spacing between the vertically-separated streamer cables 206 so that detection-zones overlap. The receiver electrodes 212 are non-polarizable (i.e., they do not produce an arbitrary battery effect or voltage offset when in use, due to corrosion and electrolysis). Thus, in a preferred embodiment, the receiver electrodes 212 are composed of silver wire immersed in a stable-base silver-chloride gel that is, in turn, exposed to contact with the seawater, but will not itself corrode. The receiver electrodes 212 are typically encased in a plastic sheath (not shown) to provide protection against abrasion and damage during deployment, while having ports or cut-outs (not shown) to still afford electrical contact with the seawater.

The pre-amplifiers or preamps 214 are standard common-mode-rejection differential pre-amplifiers. In the embodiment shown in FIG. 3, six preamps 214 are used on each streamer cable 206 to remove common-mode noise by providing each preamp 214 a reference receiver electrode equidistant between two adjacent measurement receiver electrodes (described in more detail below). Each preamp 214 is connected through electrical links 310 to the receiver electrodes 212 on either side and also to its adjoining receiver electrode 212 to implement the common-mode rejection arrangement. The preamps 214 also strengthen and condition the received signal that is returned to the ship-board control and signal processing system through the signal return cable 306 to minimize parallel-wire cross-talk. Otherwise, the two-to-$10_+$ ampere transmitted signal would overwhelm and swamp the millivolt-level signals from the receiver electrodes 212. The preamps 214 are located as close as possible to the receiver electrodes 212 to minimize the exposure to electrical streaming-potential noise, and should be compact in order to minimize the towed cross section presented by the streamer cable 206.

The array of receiver electrodes 212 on each streamer cable 206 are grouped together to form a series of dipoles or "triplets" 312 (312a-312f), with the center receiver electrode 212 of each triplet serving as a reference for the corresponding pre-amplifier 214 that sits astride the middle receiver electrode 212 of each triplet. The center preamp 214 of each triplet is a noise filter, and also amplifies and sends back up the streamer cable 206 a single received signal for that triplet. The triplets 312 sample at greater and greater distances out from the streamer cable 206 as they themselves are increasingly distant from the pair of transmitter electrodes 210. Adjacent triplets 312 can share receiver electrodes 212 at the same time because of the high input impedance of the preamps 214.

Six receiver dipoles or triplets 312 are formed with the embodiment of the invention shown in FIG. 3. More particularly, a first dipole 312a is formed by the first 212a, second 212b, and third 212c receiver electrodes 212. The second or central receiver electrode 212b in the first triplet 312a serves as the reference electrode. A second dipole 312b is formed by the second 212b, third 212c, and fourth 212d receiver electrodes 212, so that two receiver electrodes 212b, 212c are shared with the first group 312a. The third through sixth dipoles 312c-312f are formed in a similar way. This layout effectively allows sampling of the hydrocarbon plume 204 to an approximate distance up to about 2 to 3 dipole-lengths away from the streamer cable 206.

The practical maximum size for an optimal electrode-spacing is limited by how much electric transmitter current the streamer cable 206 can bear. If the dipole-spacing is too large, or the transmitted current too low, the signal from the distal receiver dipoles near the end of the streamer cable 206 can be lost or fall below the noise threshold. Making the transmitter cable 304 thicker with lower-gauge internal wires allows for transmission of greater current, but the weight of the streamer cable 206 can become prohibitive for long lengths, and this must be optimized as part of the entire survey design. The greater the transmitted current, the larger the sampling volume size (i.e., "sampling donut," described below) detected by the most distal receiver electrodes 212 and, therefore, the larger the spacing that can be permitted between the individual streamer cables 206 to still fully overlap each other and sample the entire seawater column.

The receiver triplet 312a closest to the transmitter electrodes 210 will sample a relatively small volume around it, while the receiver triplets 312b-312f further away from the transmitter electrodes 210 will sample proportionally larger volumes. When the smallest volume is subtracted from the next smallest volume, a resulting seawater capacitance number value represents the average capacitance of the ring or donut-shaped volume outside the smaller volume. This sampling-and-subtraction process can be done sequentially and automatically, providing increasingly larger "rings" or "donuts" of volume-sampling information on the capacitance of the seawater column that the streamer cable 206 is towed through. The vertical separation of the streamer cables 206 is optimized to provide overlap of the largest "volume sampling donuts" of each streamer cable, thus providing a continuous vertical volume sampling for the vertically-stacked array of streamer cables 206 as a whole.

Optimization of streamer cable 206 separations can be done experimentally or by numerical modeling, but the starting point is the type of cable that will be used for fabrication of the streamer cables 206: the number of shielded conductor-pairs or fiber-optic lines composing the signal return cable 306, their individual gauge(s), and the weight of the proposed cable per unit length. This latter consideration is important because of the limitations of the ship-board drums or spools (not shown) that are used to deploy the streamer cables 206.

Ultimately, the choice of cable—which dictates the rest of the parameters including electrode-spacing and cable separation—is dictated by what cable-type is most readily available to the fabricator, who must balance cost of components as well as shipping in the decision process. The more receiver triplets 312 there are on each streamer cable 206, the higher the vertical column sampling obtained, as long as there is sufficient transmitter current to be detected by the most-distal triplet 312f. The number of instantaneous samples obtained as the array of streamer cables is towed through the water-column is approximately the number of streamer cables 206 multiplied by the number of preamps 214 on each streamer cable 206, with some overlap. The preamps 214 are generic (including optical versus voltage output options), and there are many different commercial kinds available to design engineers, but a typical amplification factor would be at least 10.

In the exemplary embodiment shown in FIG. 3, two depth-sensing pressure transducer/acoustic transponder units 216 are located at the peripheral and distal ends of each streamer cable 206. The depth-sensing pressure transducer/acoustic transponder units 216, together with the acoustic streamer element locator 220, add precision to the location of each sampling point on each streamer cable 206 in three dimensions (latitude, longitude, and depth). The same commercially-available power supply (not shown) that feeds the preamps 214 is used to power these additional small pressure transducer/acoustic transponder units 216 on each streamer cable 206. Shipboard power supplies the 3-D acoustic streamer element locator 220 deployed from the side of the ship 202. Depth information passes up each streamer cable 206 from the depth-sensing pressure transducer/acoustic transponder units 216, and location information from the shipboard 3-D acoustic streamer element locator 220 passes independently to the control and signal processing system on the ship 202 for compilation into a 3-D image of the hydrocarbon plume 204.

The final designed vertical resolution of the entire array of streamer cables 206 is decided by engineers according to the target of interest. In other words, the number of transmitter electrodes 210 and receiver electrodes 212, the spacing between the transmitter electrodes 210 and the receiver electrodes 212, the number of streamer cables 206 used, and the depth-settings of the cable depressors 208 will all vary according to the depth of the water to be tested.

Figure 4:
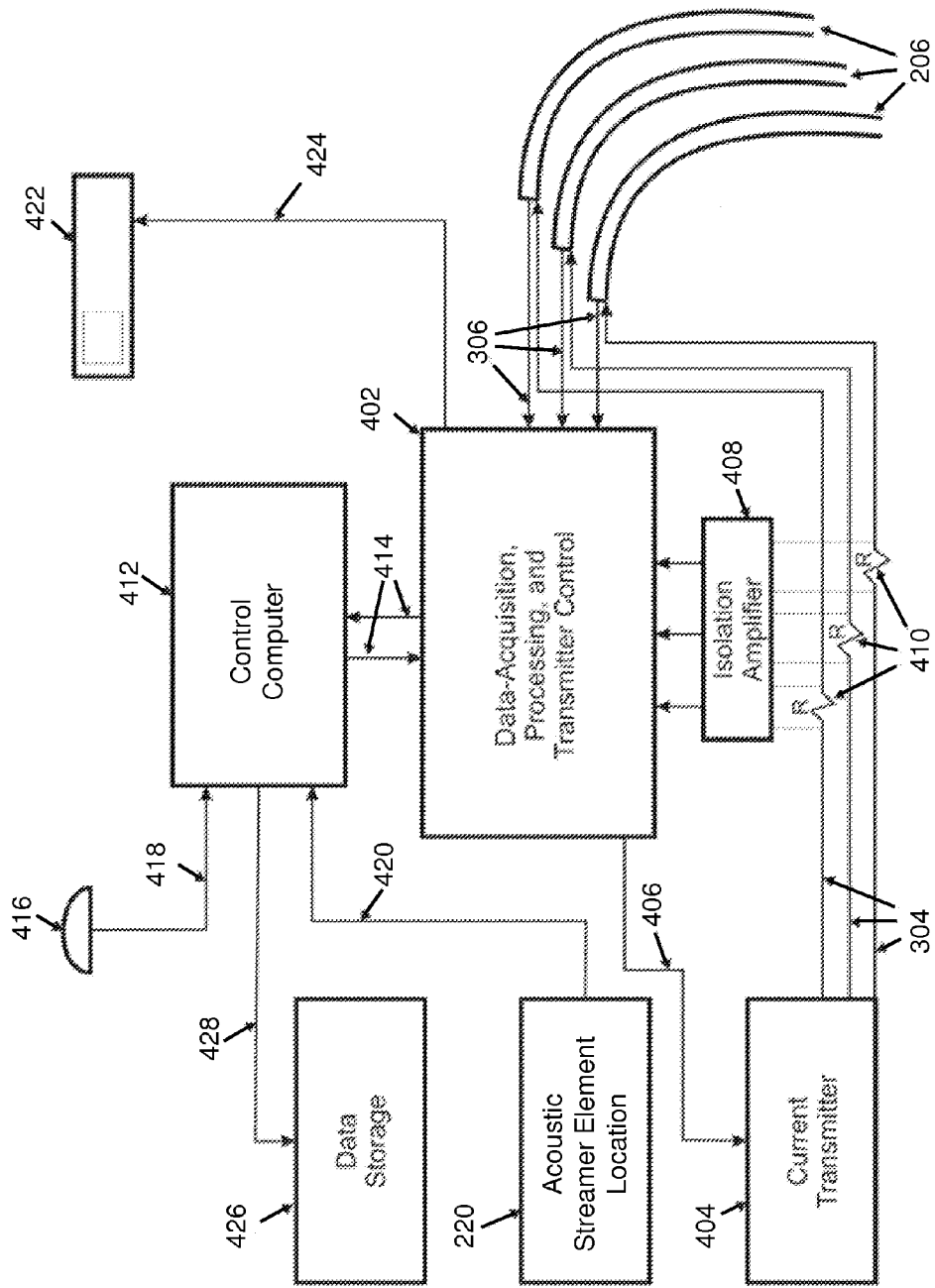
FIG. 4 is a conceptual block diagram of a control and signal processing system on board the ship of FIG. 2, according to an exemplary embodiment of the invention.

FIG. 4 shows a block diagram of the on-board control and signal processing system. In this figure, three of the streamer cables 206 are shown, as well as the transmitter cables 304 that provide current to the transmitter electrodes 210. The signal return cables 306 that carry the measured results (data) enter analog-to-digital (A/D) boards (not shown) within a multichannel data-acquisition, processing, and transmitter control unit 402. The shield surrounding each twisted-pair transmitter cable 304 is grounded 302 (see FIG. 3) and electrically isolated as much as possible to prevent cross-talk from the high-amperage transmitted signal into any received-signal links. The non-ship ground 302 is a sacrificial electrode, typically a copper plate, which is hung overboard so that the ground voltage of the on-board control and signal processing system is allowed to float independently of the electrical system of the ship 202, thereby reducing or eliminating a potent source of electrical noise contamination.

The transmitter electrodes 210 are connected through the transmitter cable 304 to a current transmitter 404. The current transmitter 404 can be a commercially-available device that is connected through a logic link 406 to the data-acquisition, processing, and transmitter control unit 402. The linkage is designed to provide a precisely-controlled, stable square wave signal to the transmitter electrodes 210. The signal return cables 306, either shielded coaxial or fiber-optic, are connected from the streamer cables 206 to the data-acquisition, processing, and transmitter control unit 402. The data-acquisition, processing, and transmitter control unit 402 is connected through an isolation amplifier 408 to transmit-signal-monitoring shunt resisters R 410 on each transmitter cable 304 twisted-pair, which are, in turn, connected to the transmitter electrodes 210 down each streamer cable 206.

A control computer 412, which in a preferred embodiment is a laptop computer or a tablet computer, is connected through a data download cable 414 to the data-acquisition, processing, and transmitter control unit 402, and also to a Differential Global Positioning System (DGPS) unit 416 through an input connection or download cable 418. Location data from the acoustic streamer locator 220 are fed to the control computer 412 through a link 420. Also, the data-acquisition, processing, and transmitter control unit 402 sends depth data from the depth-sensing pressure transducer/acoustic transponder units 216 to the control computer 412, which assembles the four-dimensional (spatial and time) sea-water capacitance map. The DGPS data stream is added to the shipboard acoustic streamer locator 220 data to precisely position the seawater capacitance results, which are the individual sampling volume donuts for each streamer cable 206, in a database in a 3-D (latitude, longitude, and depth) geographic framework with a date-time mark added for each point. Because the streamer array samples larger and larger volumes of seawater the further the receiver electrodes 212 are located from the ship 202, a simple geometric correction algorithm, as described above, is used to convert the sampling volume donut values and their overlaps to the capacitance for each particular sampled point of the hydrocarbon plume 204. The geometric correction algorithm is based upon geometric correction algorithms used in land geo-electrical surveys and can be created within the capabilities of one skilled in the art. An oscilloscope 422 is also connected by a line 424 to the data-acquisition, processing, and transmitter control unit 402 to monitor the received and transmitted signals to verify that there are no ground loops, and that no extraneous noise (e.g., 60 Hz or DC offsets from shipboard power systems) enters the data-stream.

The data acquisition, processing, and transmitter control unit 402 can be a commercially-available device, an exemplary embodiment being a 32-bit multi-channel system with individual A/D boards for each channel, along with an internal processing capability. It provides geophysical data acquisition and processing by completing Fast Fourier Transforms on the preamp waveform signals. These are deconvolved against a calibrate record (described below), which is acquired in a pollution-free area of empty sea before the data acquisition begins, to remove extraneous systemic capacitances in the return cables and the data-acquisition, processing, and transmitter control 402 hardware itself. The deconvolved waveforms of the transmitted signals measured at the shunt resistors R 410 are then subtracted to provide final signal phase-shifts for each electrode triplet 312. This is the measure of the seawater capacitance for the instantaneous volume of water sampled by each individual receiver electrode 212 of each streamer cable 206.

The isolation amplifier 408 is an isolation optical amplifier that enables the square wave signal from the current transmitter 404 to be precisely measured and instantaneously adjusted to keep it constant using feedback from the shunt resisters R 410 to the data-acquisition, processing, and transmitter control unit 402. Because the current transmitter 404 signal is optically isolated from the received signal, no electrical noise, voltage offset, or crosstalk arrives at the data-acquisition, processing, and transmitter control unit 402 from the current transmitter 404.

A system calibration is done in two stages or levels. In the first stage, after an on-board wire-harness (not shown) is set up, a series of phase and amplitude measurements are made for the on-board control and signal processing system for the full range of frequencies that will be used in the spectral mode described below, which is typically about 1 Hz to about 100 Hz. These results are Fourier transformed from the time domain to the frequency domain, and the transformed results for each frequency are stored in a data storage unit 426 connected through a link 428 to the control computer 412, where they are later deconvolved against the received signal data during actual operation. An additional second level calibration operation is done by measuring data from the entire system (including the deployed array of streamer cables) in some location at sea where there are no hydrocarbon plumes, IP-reactive minerals, or metallic objects in close proximity. The final shipboard-acquired data, with the frequency-dependent system phase-shift deconvolved therefrom in real time, are then subtracted against the second level calibration to yield systemic noise-free data.

Turning now to the operation of the system described above, the transmitter electrodes 210 of each streamer cable 206 are energized with a precisely controlled square wave voltage generated by the current transmitter 404, resulting in the injection of several amperes of electrical current into the seawater. The streamer cables 206 are pulled behind the ship 202 and are maintained at specific depths via the individual depth-control cable depressors 208 so that the hydrocarbon plume 204 is sampled simultaneously from top to bottom with precise depth information being returned for each point of data acquired. When the square wave is turned off episodically during the transmission square-wave duty-cycle, the electrochemical reaction (ion adsorption onto the oil droplet surface) reverses, and any subsequent secondary signals caused by this during transmitter off-time are detected using the non-polarizing receiver electrodes 212.

If there are no hydrocarbons present, no secondary signal will be generated. There may be electromagnetic (inductive) coupling between the transmitter electrodes 210 and the seawater, but this is constant and is automatically removed by the calibration process described above. The array of streamer cables is designed using the depth-control cable depressors 208 so that the sampling field of each individual streamer cable 206 overlaps the sampling field of the nearest overlying and underlying streamer cables 206 by about 5% to about 10% to ensure that there are no unmeasured gaps in the vertical sampling plane. Also, the spacing of the sensing or receiving electrodes 212 on each streamer cable 206 is adjusted to permit detection-overlap between the streamer cables 206. This overlap will, in turn, be dictated by the number of streamer cables 206 that are deployed simultaneously in a given vertical stack of streamer cables and by the amount of transmitter current the streamer cable 206 can tolerate without overheating and becoming damaged.

While underway, the streamer cables 206 cut through the seawater column and intersect any plumes or plume stringers 204, providing a real-time reading on the location of the oil at multiple depths in a two-dimensional vertical plane. The data are acquired very rapidly at a single square-wave frequency (which by Fast Fourier Transform is converted to its individual harmonics), typically with a fundamental ($1^{st}$ harmonic) frequency of 1-4 Hz, in a continuous sampling mode at typical towing speeds of about 3 knots or higher. A very large area can thus be covered in this manner in a very short time, limited by how fast the ship 202 can move and still maintain the cable depressors 208 at a fixed depth.

The ship 202 makes a pass across the region of interest, and then makes a so-called "keyhole turn." The tow-path is thus offset and folded over and parallel to itself, back and forth, to cover a large surface area on the sea and, thus, sample a large volume beneath the sea. Each towed-path sampling plane, which is a tall but narrow sampling volume, is parallel to previous sampling planes, the aggregate providing a rapid full volume of sampling over a wide area and the full depth range being searched for the hydrocarbon or hydrocarbon-and-dispersant plumes. This permits the assembly of a three-dimensional picture of both hydrocarbon density and droplet size, providing in aggregate the plume location and three-dimensional shape, as well as the droplet-size distribution. The survey can be repeated on subsequent days to determine how the plume is moving and evolving with time. This would then give scientists a predictive capability for future plume movement, as well as plume degradation rates (which are seen as a change in the frequency distribution of the measured seawater capacitance), which also contribute toward predicting its future location and state.

An alternative to the way in which the streamer cables 206 are towed behind the ship 202 is to have a robust sled (not shown) running at the top of the expected plume 204 depth.

From this sled, multiple streamer cables 206 with depth-control cable-depressors 208 would be deployed. The sled would have much of the ship-board electronics for data-processing and current transmission.

There are also other geometrical alternatives to the seawater-sampling array. For example, a single, long master cable can reach down from the ship to great depth to a heavy, powered sled or remotely-operated vehicle that would track beneath the towing ship and turn with it. Multiple transmitter-receiver sets (i.e., parasitic cables) would be distributed down the main cable, each parasitic cable extending off and behind the master towed main cable, trailing in the sea in the direction opposite the direction of tow, each making its own measurements at different depths. These measurement results would all be collected simultaneously to assemble a near real-time, 3-dimensional picture of the location and state of the hydrocarbon plume. There would be only a single depth-sensing transducer required for each parasitic cable, and as few as a single pair of transmitter electrodes and a single triplet or non-polarizing receiver electrodes on each cable. A preamplifier would be used on each parasitic cable.

The present invention provides a near real-time approach to map and characterize hydrocarbon plumes 204 from major oil well blowouts and pipeline leaks, as well as from natural oil seeps. It does not require time-consuming drop sampling or chemical analyses of seawater pollutants, though lab-sampling of representative oil-saltwater mixes beforehand will increase its predictive accuracy. The related IP approach has previously been used to map minerals fixed in place beneath the land or seafloor. The streamer array of the present invention maps a moving target in the sea in four dimensions. In other words, the seawater capacitance measuring system and method described herein allows for the mapping and characterization (i.e., depth, thickness, density, droplet size, etc.) of the hydrocarbon plume, including its volume distribution in the open ocean, and how it evolves (i.e., moves and degrades) with time.

Although the present invention has been described relative to specific exemplary embodiments thereof, it will be understood by those skilled in the art that variations and modifications can be effected in these exemplary embodiments without departing from the scope and spirit of the invention.

What is claimed is:

1. A seawater capacitance detection method for rapidly mapping and characterizing hydrocarbon plumes in seawater, the method comprising:

towing a streamer array having three or more vertically stacked streamer cables at three or more depths, respectively, through a seawater column containing a hydrocarbon plume;

energizing two or more transmitter electrodes on each streamer cable with an electrical current signal, the transmitter electrodes injecting electrical current into the seawater column;

episodically turning off transmission of the electrical current signal;

arranging a plurality of receiver electrodes on each streamer cable into one or more receiver sets, each receiver set sampling a volume of seawater surrounding it and detecting any returned secondary signals produced by a capacitive effect resulting from injecting the electrical current into the seawater column and turning off the transmission of the electrical current signal, and each receiver set successively sampling a larger volume of water as the receiver sets are positioned further away from the transmitter electrodes;

processing the returned secondary signals, for each adjacent pair of receiver sets, by subtracting the smallest volume of seawater from the next smallest volume of seawater to yield a capacitance value of a donut-shaped sampling volume of seawater outside the smallest volume, the receiver sets positioned further away from the transmitter electrodes providing increasingly larger donut-shaped sampling volumes of sampling data of the capacitance of the seawater column through which the streamer cables are towed;

processing and geometrically correcting the capacitance values of the donut-shaped sampling volumes of seawater to yield a frequency-varying final seawater capacitance value for the volume of seawater sampled by each receiver set; and mapping and characterizing the hydrocarbon plume using the final seawater capacitance values of the receiver sets.

2. The seawater capacitance detection method of claim 1, wherein said arranging a plurality of receiver electrodes on each streamer cable into one or more receiver sets comprises arranging eight or more receiver electrodes in groups of three to form six or more triplets, each adjacent pair of triplets sharing two receiver electrodes.

3. The seawater capacitance detection method of claim 1, wherein said processing and geometrically correcting the capacitance values of the donut-shaped sampling volumes of seawater to yield a frequency-varying final seawater capacitance value for the volume of seawater sampled by each receiver set comprises measuring a phase shift between the transmitted electrical current signal and the processed returned secondary signals detected by each receiver set.

4. The seawater capacitance detection method of claim 1, further comprising optimizing vertical separation between the vertically stacked streamer cables by providing overlap of the donut-shaped sampling volumes of seawater sampled by the receiver sets of each streamer cable to provide continuous vertical volume sampling for the vertically stacked array of streamer cables as a whole.

5. The seawater capacitance detection method of claim 1, wherein said towing a streamer array having three or more vertically stacked streamer cables at three or more depths, respectively, through a seawater column further comprises maintaining each streamer cable at a specific depth so that a sampling field of each streamer cable overlaps a sampling field of adjacent overlying and underlying streamer cables by about 5 percent to about 10 percent to remove any unmeasured gaps in a vertical sampling plane.

6. The seawater capacitance detection method of claim 1, wherein said energizing two or more transmitter electrodes on each streamer cable with an electrical current signal further comprises energizing the transmitter electrodes with a square wave current signal and optimizing a waveform of the square wave current signal to include constituent frequencies in the range of about 1 Hz to about 100 Hz, and using the constituent frequencies to detect the frequency-varying final seawater capacitance values of discrete parts of the hydrocarbon plume in the seawater.

7. The seawater capacitance detection method of claim 1, wherein said mapping and characterizing the hydrocarbon plume using the final seawater capacitance values of the receiver sets further comprises:

obtaining spatial data by obtaining depth and location data for each streamer cable to precisely locate each sampling point on each streamer cable and provide an image of the hydrocarbon plume in three dimensions including latitude, longitude, and depth;

measuring movement of the hydrocarbon plume over time;

comparing characteristics of known hydrocarbons and hydrocarbon-saltwater mixes to measured characteristics of the hydrocarbon plume to precisely characterize the hydrocarbon plume; and using the spatial, time, and characterization data and a frequency distribution of the capacitance values over a plurality of frequency decades to assemble a four-dimensional seawater capacitance map that includes hydrocarbon plume density and droplet-size distribution of oil droplets that form the hydrocarbon plume, the four-dimensional seawater capacitance map providing the ability to predict future hydrocarbon plume location and state.

8. The seawater capacitance detection method of claim 1, wherein said towing a streamer array having three or more vertically stacked streamer cables at three or more depths, respectively, through a seawater column further comprises towing the streamer cables by a ship across a region of interest by making keyhole turns to create a tow-path that is offset and folded over and parallel to itself, back and forth, and each towed path forming a sampling plane that is parallel to previous sampling planes.

9. A seawater capacitance detection method for rapidly mapping and characterizing hydrocarbon plumes in seawater, the method comprising:
   towing a streamer array having three or more vertically stacked streamer cables at three or more depths, respectively, through a seawater column;
   placing two or more transmitter electrodes and a plurality of receiver electrodes on each streamer cable;
   transmitting, by the transmitter electrodes, an electrical current into the seawater;
   episodically terminating transmission of the electrical current signal;
   measuring, by the receiver electrodes, returned secondary signals produced in response to terminating transmission of the electrical current signal, a non-zero capacitance value of the returned secondary signals indicating the presence of a hydrocarbon plume in the seawater;
   calculating, based on the returned secondary signals, a capacitance value for discrete volume points within the hydrocarbon plume and seawater mixture sampled by the receiver electrodes; and
   mapping and characterizing the hydrocarbon plume using the capacitance values.

10. The seawater capacitance detection method of claim 9, wherein said transmitting, by the transmitter electrodes, an electrical current into the seawater comprises transmitting a square wave current signal into the seawater.

11. The seawater capacitance detection method of claim 10, wherein said transmitting a square wave current signal into the seawater comprises optimizing a waveform of the square wave current signal to include constituent frequencies in the range of about 1 Hz to about 100 Hz, and using the amplitudes of each constituent frequency extracted by Fourier transform to detect the frequency-varying final seawater capacitance values of the hydrocarbon plume and seawater mixture sampled by the receiver electrodes.

12. The seawater capacitance detection method of claim 9, where said placing two or more transmitter electrodes and a plurality of receiver electrodes on each streamer cable comprises arranging the receiver electrodes on each streamer cable into one or more receiver sets, each receiver set sampling a volume of seawater surrounding it, and each receiver set successively sampling a larger volume of water as the receiver sets are positioned further away from the transmitter electrodes.

13. The seawater capacitance detection method of claim 12, wherein said arranging the receiver electrodes on each streamer cable into one or more receiver sets comprises arranging eight or more receiver electrodes in groups of three to form six or more triplets, each adjacent pair of triplets sharing two receiver electrodes.

14. The seawater capacitance detection method of claim 12, wherein said measuring, by the receiver electrodes, returned secondary signals produced in response to terminating transmission of the electrical current signal comprises processing the returned secondary signals, for each adjacent pair of receiver sets, by subtracting the smallest volume of seawater sampled by the nearest triplet from the next smallest volume of seawater to yield a capacitance value of a donut-shaped sampling volume of seawater outside the smallest volume, the receiver sets positioned further away from the transmitter electrodes providing increasingly larger donut-shaped sampling volumes of sampling data of the capacitance of the seawater column through which the streamer cables are towed.

15. The seawater capacitance detection method of claim 14, wherein said calculating, based on the returned secondary signals, a capacitance value for discrete volume points within the hydrocarbon plume and seawater mixture sampled by the receiver electrodes comprises geometrically correcting the capacitance value by measuring a phase shift between the transmitted electrical current signal and the processed returned secondary signals.

16. The seawater capacitance detection method of claim 15, wherein said measuring a phase shift between the transmitted electrical current signal and the processed returned secondary signals comprises:
   performing a calibration measurement of ship-board instrumentation on a ship towing the streamer array to permanently remove a phase contribution from the ship-board instrumentation, the calibration measurement yielding a first measured calibration signal;
   performing a calibration measurement of a phase contribution of the ship and the streamer array in a hydrocarbon-free ocean to yield a second measured calibration signal;
   performing a Fast Fourier Transform on the first and the second measured calibration signals to yield a system measured calibration signal;
   performing a Fast Fourier Transform on the processed returned secondary signals;
   deconvolving the Fourier-transformed returned secondary signals against the system measured calibration signal; and
   deconvolving the frequency domain results of the transmitted electrical current signals frequency-by-frequency from the Fourier-transformed returned secondary signals to yield the capacitance values between the hydrocarbon plume and the seawater for each receiver electrode triplet.

17. The seawater capacitance detection method of claim 14, further comprising optimizing vertical separation between the vertically stacked streamer cables by providing overlap of the donut-shaped sampling volumes of seawater sampled by the receiver sets of each streamer cable to provide a continuous vertical volume sampling for the vertically stacked array of streamer cables as a whole.

18. The seawater capacitance detection method of claim 9, wherein said transmitting an electrical current into the seawater polarizes a mixture of the hydrocarbon plume and the seawater.

19. The seawater capacitance detection method of claim 14, wherein said mapping and characterizing the hydrocarbon plume in the seawater column using the capacitance values further comprises:
- obtaining spatial data by obtaining depth and location data for each streamer cable to precisely locate each sampling point on each streamer cable and provide an image of the hydrocarbon plume in three dimensions including latitude, longitude, and depth;
- measuring movement of the hydrocarbon plume over time;
- using the spatial and time data to assemble a four-dimensional seawater capacitance map that includes hydrocarbon plume density and droplet-size distribution of oil droplets that form the hydrocarbon plume, the four-dimensional seawater capacitance map providing the ability to predict future hydrocarbon plume location and state; and
- characterizing the hydrocarbon plume according to droplet size from discrete capacitance frequency distributions for each sampling volume as the hydrocarbon plume evolves over time.

20. The seawater capacitance detection method of claim 9, wherein said towing a streamer array having three or more vertically stacked streamer cables at three or more depths, respectively, through seawater further comprises controlling vertical placement of each streamer cable to maintain each streamer cable at a specific depth so that a sampling field of each streamer cable overlaps a sampling field of adjacent overlying and underlying streamer cables by about 5 percent to about 10 percent to remove any unmeasured gaps in a vertical sampling plane.

21. The seawater capacitance detection method of claim 9, wherein said towing a streamer array having three or more vertically stacked streamer cables at three or more depths, respectively, through seawater further comprises towing the streamer cables by a ship across a region of interest by making keyhole turns to create a tow-path that is offset and folded over and parallel to itself, back and forth, and each towed path forming a sampling plane that is parallel to previous sampling planes.

22. A seawater capacitance detection method for rapidly mapping and characterizing hydrocarbon plumes in seawater, the method comprising:
- towing a master streamer cable through a seawater column;
- attaching a sled to an end of the master streamer cable to maintain it substantially vertical in the seawater column;
- attaching a plurality of parasitic streamer cables to the master streamer cable, each parasitic streamer cable extending from the master streamer cable and sampling different depths simultaneously;
- placing two or more transmitter electrodes and a plurality of receiver electrodes on each parasitic streamer cable;
- transmitting, by the transmitter electrodes, an electrical current into the seawater;
- episodically terminating transmission of the electrical current signal;
- measuring, by the receiver electrodes, returned secondary signals produced in response to terminating transmission of the electrical current signal, a non-zero capacitance value of the returned secondary signals indicating the presence of a hydrocarbon plume in the seawater;
- calculating, based on the returned secondary signals, a capacitance value for discrete volume points within the hydrocarbon plume and seawater mixture sampled by the receiver electrodes; and
- mapping and characterizing the hydrocarbon plume using the capacitance values.

* * * * *